US00PP30206P3

(12) United States Plant Patent
Barnes

(10) Patent No.: US PP30,206 P3
(45) Date of Patent: Feb. 12, 2019

(54) ***SALVIA* PLANT NAMED 'BBSAL09001'**

(50) Latin Name: *Salvia hybrida*
Varietal Denomination: BBSAL09001

(71) Applicant: Brent D. Barnes, Riverside, CA (US)

(72) Inventor: Brent D. Barnes, Riverside, CA (US)

(73) Assignee: Plant 21 LLC, Bonsall, CA (US)

( * ) Notice: Subject to any disclaimer, the term of this patent is extended or adjusted under 35 U.S.C. 154(b) by 16 days.

(21) Appl. No.: 15/731,521

(22) Filed: Jun. 21, 2017

(65) Prior Publication Data

US 2018/0376645 P1 Dec. 27, 2018

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

(56) References Cited

PUBLICATIONS

UPOV hit on *Salvia* plant named 'BBSAL09001', Ca PBR 17-9133, filed Mar. 16, 2017.*

* cited by examiner

*Primary Examiner* — Anne Marie Grunberg
(74) *Attorney, Agent, or Firm* — C. A. Whealy

(57) ABSTRACT

A new and distinct cultivar of *Salvia* plant named 'BBSAL09001', characterized by its upright plant habit; moderately vigorous to vigorous growth habit; freely branching habit; strong dark purple-colored lateral branches; dark green-colored leaves; early and freely flowering habit; upright inflorescences with dark violet-colored flowers with dark violet blue-colored sepals; and good garden performance.

1 Drawing Sheet

Botanical designation: *Salvia hybrida.*
Cultivar denomination: 'BBSAL09001'.

BACKGROUND OF THE INVENTION

The present invention relates to a new and distinct cultivar of *Salvia* plant, botanically known as *Salvia hybrida* and hereinafter referred to by the name 'BBSAL09001'.

The new *Salvia* plant is a product of a planned breeding program conducted by the Inventor in Bonsall, Calif. The objective of the breeding program is to create new uniform *Salvia* plants with attractive leaves and flowers.

The new *Salvia* plant originated from a cross-pollination of a proprietary selection of *Salvia hybrida* identified as code number 14SJ001-01, not patented, as the female, or seed, parent with a proprietary selection of *Salvia hybrida* identified as code number 13SALB040-01, not patented, as the male, or pollen, parent on Oct. 13, 2014. The new *Salvia* plant was discovered and selected by the Inventor as a single flowering plant from within the progeny of the stated cross-pollination in a controlled greenhouse environment in Bonsall, Calif. on Dec. 29, 2014.

Asexual reproduction of the new *Salvia* plant by vegetative terminal cuttings in Bonsall, Calif., since Jan. 14, 2015 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBSAL09001'. These characteristics in combination distinguish 'BBSAL09001' as a new and distinct *Salvia* plant:

1. Upright plant habit.
2. Moderately vigorous to vigorous growth habit.
3. Freely branching habit.
4. Strong dark purple-colored lateral branches.
5. Dark green-colored leaves.
6. Early and freely flowering habit.
7. Upright inflorescences with dark violet-colored flowers with dark violet blue-colored sepals.
8. Good garden performance.

Plants of the new *Salvia* can be compared to plants of the female parent selection. Plants of the new *Salvia* differ primarily from plants of the female parent selection in the following characteristics:

1. Plants of the new *Salvia* are more freely branching and denser than plants of the female parent selection.
2. Plants of the new *Salvia* have stronger and sturdier lateral branches than plants of the female parent selection.
3. Plants of the new *Salvia* have longer flowers than plants of the female parent selection.

Plants of the new *Salvia* can be compared to plants of the male parent selection. Plants of the new *Salvia* differ primarily from plants of the male parent selection in the following characteristics:

1. Plants of the new *Salvia* are more compact than plants of the male parent selection.
2. Plants of the new *Salvia* and the male parent selection differ in flower color as plants of the male parent selection have pale blue-colored flowers.
3. Plants of the new *Salvia* flower for a longer period of time than plants of the male parent selection.

Plants of the new *Salvia* can be compared to plants of *Salvia hybrida* 'Amistad', disclosed in U.S. Plant Pat. No. 23,578. In side-by-side comparisons, plants of the new *Salvia* differ from plants of 'Amistad' in the following characteristics:

1. Plants of the new *Salvia* are more compact and upright in plant habit than plants of 'Amistad'.
2. Plants of the new *Salvia* are more freely branching and denser than plants of 'Amistad'.
3. Plants of the new *Salvia* have stronger and sturdier lateral branches than plants of 'Amistad'.
4. Plants of the new *Salvia* have darker green-colored leaves than plants of 'Amistad'.

Plants of the new *Salvia* can also be compared to plants of *Salvia guaranitica* 'Black and Blue', not patented. In side-by-side comparisons, plants of the new *Salvia* differ from plants of 'Black and Blue' in the following characteristics:

1. Plants of the new *Salvia* are more freely branching and denser than plants of 'Black and Blue'.
2. Plants of the new *Salvia* flower earlier than plants of 'Black and Blue'.
3. Plants of the new *Salvia* and 'Black and Blue' differ in flower color as plants of 'Black and Blue' have blue-colored flowers.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the actual colors of the new *Salvia* plant.

The photograph at the top of the sheet is a side perspective view of a typical flowering plant of 'BBSAL09001' grown in a container.

The photograph at the bottom of the sheet is a close-up view of a typical flowering plant of 'BBSAL09001'.

DETAILED BOTANICAL DESCRIPTION

The aforementioned photographs and following observations and measurements describe plants grown during the early spring in 11.5-cm containers in an acrylic-covered greenhouse in Carleton, Mich. and under cultural practices typical of commercial *Salvia* production. During the production of the plants, day and night temperatures ranged from 18° C. to 27° C. Plants were twelve weeks from planting rooted cuttings when the photographs and description were taken. In the following description, color references are made to The Royal Horticultural Society Colour Chart, 2007 Edition, except where general terms of ordinary dictionary significance are used.

Botanical classification: *Salvia hybrida* 'BBSAL09001'.

Parentage:

*Female, or seed, parent.*—Proprietary selection of *Salvia hybrida* identified as code number 14SJ001-01, not patented.

*Male, or pollen, parent.*—Proprietary selection of *Salvia hybrida* identified as code number 13SALB050-01, not patented.

Propagation:

*Type.*—By vegetative terminal cuttings.

*Time to initiate roots, summer.*—About four to five days at temperatures about 17° C. to 29° C.

*Time to initiate roots, winter.*—About seven to nine days at temperatures about 17° C. to 21° C.

*Time to produce a rooted young plant, summer.*—About three to four weeks at temperatures about 17° C. to 29° C.

*Time to produce a rooted young plant, winter.*—About four to five weeks at temperatures about 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial typically grown as a container and garden plant; upright plant habit; uniform and moderately vigorous to vigorous growth habit; rapid growth rate.

*Branching habit.*—Freely basal branching with about six primary lateral branches per plant; dense appearance.

*Plant height, soil level to top of foliar plane.*—About 20 cm.

*Plant height, soil level to top of floral plane.*—About 31 cm.

*Plant width.*—About 36 cm.

*Lateral branch description.*—Length: About 22 cm. Diameter: About 6 mm. Internode length: About 4.5 cm to 5 cm. Strength: Strong and sturdy. Aspect: Mostly upright to about 45° to 60° from vertical. Texture and luster: Pubescent; matte. Color, developing: Close to 146A to 146B. Color, developed: Close to N187A.

Leaf description:

*Arrangement.*—Opposite, simple.

*Length.*—About 7.5 cm.

*Width.*—About 5.5 cm.

*Shape.*—Broadly lanceolate to nearly deltoid.

*Apex.*—Acute.

*Base.*—Attenuate.

*Margin.*—Crenate.

*Texture and luster, upper surface.*—Fine pubescence, slightly rough; slightly glossy.

*Texture, lower surface.*—Fine pubescence, somewhat coarse; matte.

*Venation pattern.*—Pinnate, reticulate.

*Color.*—Developing leaves, upper and lower surfaces: Close to 144A. Fully expanded leaves, upper surface: Close to N137A; venation, close to 146B. Fully expanded leaves, lower surface: Close to 146A; venation, close to 147C.

*Petioles*.—Length: About 4.3 cm. Diameter: About 2.5 mm. Strength: Strong. Texture and luster, upper and lower surfaces: Minute pubescence; matte. Color, upper surface: Close to 146A. Color, lower surface: Close to 146B.

Flower description:

*Flower arrangement and shape*.—Single bilabiate flowers arranged on erect terminal and axillary racemes; freely flowering habit with about 95 flowers developing per inflorescence and more than 850 flowers developing per plant during the flowering season; flowers face upward to mostly outwardly.

*Fragrance*.—None detected.

*Natural flowering season*.—Early flowering habit, plants begin flowering about six weeks after planting; plants flower from spring until frost in an outdoor nursery in Michigan.

*Flower longevity*.—Flowers last about four to five days on the plant; flowers not persistent.

*Flower buds*.—Length: About 3.4 cm. Diameter: About 8 mm. Shape: Elongate. Texture and luster: Minute scattered pubescence; matte. Color: Close to N92C.

*Inflorescence height*.—About 16 cm.

*Inflorescence diameter*.—About 8 cm.

*Flower diameter*.—About 1.2 cm.

*Flower length*.—About 3 mm by 5 mm.

*Flower throat diameter*.—About 3 mm by 5 mm.

*Flower tube length*.—About 2.7 cm.

*Petals*.—Arrangement: Five petals with two upper petals fused forming a galea and three lower petals fused forming a broader lower protruding lip. Upper galea length: About 2 cm. Upper galea width: About 5 mm. Lower lip length: About 1.4 cm. Lower lip width: About 1.2 cm. Shape: Upper galea, hooded; lower lip, rounded. Apex: Round. Base: Fused into a narrow tube. Margin: Entire. Texture and luster, upper surface: Smooth, glabrous; matte. Texture and luster, lower surface: Minute pubescence; slightly glossy. Texture and luster, throat: Smooth, glabrous; matte. Texture and luster, tube: Sparsely pubescent; slightly glossy. Color: When opening, upper surface: Close to 83A. When opening, lower surface: Close to N92B. Fully opened, upper surface: Close to 83A to 83B; venation, close to 83A; color does not fade with development. Fully opened, lower surface: Close to 86A; venation, close to 86A; color does not fade with development. Throat: Close to 86C; venation, close to 86C. Tube: Close to 83A; venation, close to 83A.

*Calyx*.—Arrangement: Five sepals fused to form a tubular bilabiate calyx. Length: About 6 mm. Width: About 7 mm. Shape: Roughly lanceolate. Apex: Acute. Margin: Entire. Texture and luster, inner surface: Smooth, glabrous; matte. Texture and luster, outer surface: Scattered pubescence; matte. Color: When developing, inner and outer surfaces: Close to N92A. Fully developed, inner and outer surfaces: Close to N92A.

*Peduncles*.—Length: About 4.5 cm. Diameter: About 5 mm. Strength: Strong. Aspect: Mostly erect to about 45° to 55° from vertical. Texture and luster: Sparsely pubescent; matte. Color: Close to N92A.

*Pedicels*.—Length: About 4 mm. Diameter: About 1 mm. Strength: Strong, flexible. Aspect: About 30° to 55° from vertical. Texture and luster: Fine pubescence; matte. Color: Close to N92A.

*Reproductive organs*.—Stamens: Quantity per flower: Two. Filament length: About 1.2 cm. Filament color: Close to 91B. Anther shape: Lanceolate. Anther size: About 1 mm by 4 mm. Anther color: Close to 83A. Pollen amount: Scarce. Pollen color: Close to 155A. Pistils: Quantity per flower: One. Pistil length: About 4.4 cm. Stigma shape: Bipartite. Stigma color: Close to 86A. Style length: About 4 cm. Style color: Close to 91A, 91B and 91C. Ovary color: Close to 157A.

*Seeds and fruits*.—Seed and fruit production has not been observed on plants of the new *Salvia* to date.

Disease & pest resistance: Plants of the new *Salvia* have not been noted to be resistant to pathogens and pests common to *Salvia* plants.

Garden performance: Plants of the new *Salvia* have exhibited good garden performance and to be tolerant to rain, wind, low temperatures about 2° C. and to be suitable for USDA Hardiness Zone 10.

It is claimed:

1. A new and distinct *Salvia* plant named 'BBSAL09001' as illustrated and described.

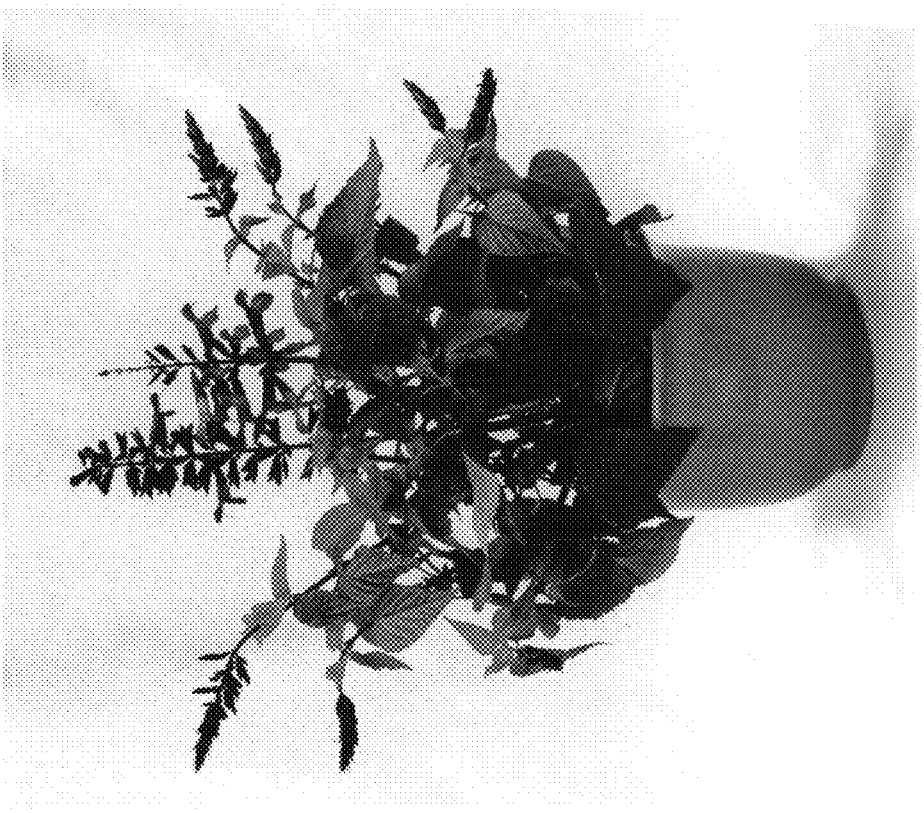
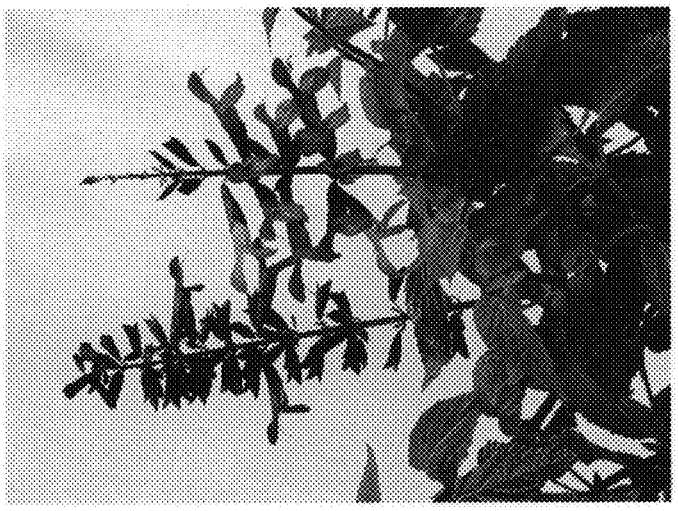

* * * * *